United States Patent [19]
Falb et al.

[11] Patent Number: 5,235,971
[45] Date of Patent: Aug. 17, 1993

[54] ANESTHETIC METERING DEVICE

[75] Inventors: Wolfgang Falb, Krummesse; Karl-Ludwig Gippert; Ulrich Heim, both of Lübeck; Uvo Hölscher, Stockelsdorf; Siegfried Kiske, Krimmesse; Götz Kullik, Lübeck; Ralf-Ernst Löser, Kreuzkamp; Christoph Maurer, Bad Schwartau, all of Fed. Rep. of Germany

[73] Assignee: Drägerwerk Aktiengesellschaft, Lubweck, Fed. Rep. of Germany

[21] Appl. No.: 833,325

[22] Filed: Feb. 10, 1992

[30] Foreign Application Priority Data

Feb. 26, 1991 [DE] Fed. Rep. of Germany ....... 4105972

[51] Int. Cl.⁵ .............................................. A61M 16/01
[52] U.S. Cl. .......................... 128/203.14; 128/204.22; 128/204.21; 128/203.12
[58] Field of Search ....................... 128/202.22, 203.12, 128/203.14, 203.25, 203.26, 203.27, 204.22, 204.21, 911, 912, 205.11

[56] References Cited

U.S. PATENT DOCUMENTS

| | | | |
|---|---|---|---|
| 3,351,057 | 11/1967 | Goodyear | 128/203.12 X |
| 3,362,404 | 1/1968 | Beasley | 128/204.14 X |
| 3,536,088 | 10/1970 | Moyat | 128/203.14 X |
| 3,566,865 | 3/1971 | Hay | 128/203.14 |
| 4,587,967 | 5/1986 | Chu | 128/204.21 |
| 4,611,590 | 9/1986 | Ryschka | 128/203.14 |
| 4,750,483 | 6/1988 | Ankartross | 128/203.25 |
| 4,770,168 | 9/1988 | Rusz | 128/203.12 |
| 4,798,689 | 1/1989 | Heim | 261/39.1 |
| 5,049,317 | 9/1991 | Kiske | 261/16 |
| 5,094,235 | 3/1992 | Westenskow | 128/204.22 |
| 5,146,915 | 9/1992 | Montgomery | 128/203.14 |
| 5,168,866 | 12/1992 | Montgomery | 128/203.12 |

FOREIGN PATENT DOCUMENTS

| | | | |
|---|---|---|---|
| 375845 | 7/1990 | European Pat. Off. | 128/205.11 |
| 2561927 | 10/1985 | France | 128/205.11 |
| 8501824 | 1/1987 | Netherlands | 128/203.12 |
| 766606 | 9/1980 | U.S.S.R. | 128/203.14 |
| 965432 | 10/1982 | U.S.S.R. | 128/203.12 |
| 2150034 | 6/1985 | United Kingdom | 128/203.12 |
| 2226763 | 7/1990 | United Kingdom | 128/205.11 |

Primary Examiner—Edgar S. Burr
Assistant Examiner—Eric P. Raciti
Attorney, Agent, or Firm—McGlew and Tuttle

[57] ABSTRACT

An anesthetic metering device is provided with a temperature-stabilized anesthetic vapor source, from which anesthetic vapor 14 is metered into a carrier gas stream via a delivery line 8 with a metering valve 11 that can be controlled by a control unit 6. The arrangement is provided so that uncontrolled evaporation of anesthetic is prevented. To accomplish this task, the anesthetic vapor source is designed as a vaporizer chamber 2 filled with liquid anesthetic 3, and a gas delivery element 9 generating the metering pressure $P_I$ is present in front of the metering valve 11.

16 Claims, 3 Drawing Sheets

ANESTHETIC METERING DEVICE

FIELD OF THE INVENTION

The present invention pertains to an anesthetic metering device with a temperature-stabilized anesthetic vapor source, from which anesthetic vapor is metered into a carrier gas stream via a delivery line with a metering valve that can be driven by a control unit.

BACKGROUND OF THE INVENTION

An anesthetic metering device of the above-described class has become known from EP-A2-231,513. The prior-art anesthetic metering device consists of a reservoir, from which liquid anesthetic is pressed by a delivery pressure into a heated vaporizer chamber serving as an anesthetic vapor source. The pressurized anesthetic vapor is metered via a cyclically operating metering valve into a carrier gas stream, e.g., an oxygen-laughing gas mixture, and sent to an anesthetic apparatus. Corresponding to the pressure in the vaporizer chamber, the degree of opening of the metering valve, and the volume flow of the carrier gas per unit time, a corresponding anesthetic concentration becomes established in the carrier gas stream.

One disadvantage of the prior-art anesthetic metering device is the fact that if the heating of the vaporizer chamber is insufficient, e.g., in the case of malfunction of the heater, liquid anesthetic may enter the carrier gas stream, leading to a considerable increase in concentration there.

Malfunction of the metering valve would also cause an abrupt entry of the anesthetic vapor present in the vaporizer chamber into the carrier gas stream. Another disadvantage is the fact that the delivery pressure in the reservoir is difficult to set to a stable value in the case of low-boiling anesthetics, as a result of which the volume of liquid anesthetic flowing per unit time into the vaporizer chamber is subject to variations, because the vapor pressure acts in addition to the delivery pressure.

An anesthetic metering device known from DE-C2,31,16,951 provides for delivery of liquid anesthetic with a pump from a reservoir into a heated vaporizer chamber, where it is completely mixed into the carrier gas stream flowing through the vaporizer chamber.

One disadvantage of the prior-art device is the fact that an increased amount of liquid anesthetic enters the vaporizer chamber in the case of malfunction of the pump, and leads to an uncontrolled increase in the anesthetic concentration in the carrier gas stream there.

SUMMARY AND OBJECTS OF THE INVENTION

It is a primary object of the present invention to improve an anesthetic metering device so that an uncontrolled evaporation of liquid anesthetic in the anesthetic vapor source is prevented, and the accuracy of metering is improved.

To attain this object, the anesthetic vapor source is designed as a vaporizer chamber filled with liquid anesthetic, and a gas delivery element generating the metering pressure $P_I$ is located in front of the metering valve.

The advantage of the present invention essentially lies in the fact that the liquid anesthetic is no longer delivered into the vaporizer chamber, where it will evaporate more or less completely, but the anesthetic is metered solely from the anesthetic vapor volume present above the liquid anesthetic. To achieve this, liquid anesthetic is filled into the vaporizer chamber, and the anesthetic vapor being formed is pumped off by the gas delivery element, and adjusted to the metering pressure $P_I$ in front of the metering valve. If the metering valve is designed as a digital valve, the amount of anesthetic vapor in the carrier gas stream is adjusted by the opening, which is limited in time, and which may also take place as repeated pulse-like openings. If, in contrast, the metering valve is designed as an analog valve, a degree of opening which is obtained from the amount of anesthetic vapor to be metered is set on the analog valve.

Thus, it is advantageous to design the gas delivery element as a pump with a downstream buffer volume and to arrange a pressure transducer in the buffer volume to detect an actual value signal of the metering pressure $P_I$, with which a metering pressure regulated quantity signal for the pump is formed in a metering pressure regulator. The metering pressure regulator is also connected to the control unit and receives the metering pressure set value $P_S$ from there. In conjunction with the degree of opening and the opening time t of the metering valve, the metering pressure $P_I$ is a measure for the volume of anesthetic vapor metered per unit time into the carrier gas stream. To prevent anesthetic from condensing, it is advantageous to heat the pipe between the vaporizer chamber and the metering valve, the pump, and the buffer volume.

According to another advantageous embodiment, the pump and the buffer volume are designed as a modular unit as a piston or bellows type pump. An intake valve, which, being a directional valve, permits gas to flow only from the vaporizer chamber to the metering valve, is provided on the suction side. The movable pump part of the bellows pump or piston pump is driven by a pump drive, and an ejection force is applied to it during the ejection phase, so that the metering pressure $P_I$ is present in front of the metering valve. If the ejection takes place with constant ejection force, a constant metering pressure $P_I$ will become established. However, it is also possible not only to meter the anesthetic vapor on the basis of the metering pressure $P_I$ and the opening time t of the metering valve, but also to meter the volume of anesthetic vapor delivered by the movable pump part directly into the carrier gas stream. To do so, the metering valve is controlled by the control unit so that it is in the closed position during the suction phase and in the open position during the ejection phase. The pump stroke is measured with a displacement transducer. A delivery pressure $P_F$ now becomes established in the piston pump. The volume of anesthetic vapor delivered per unit time is proportional to the product of the delivery pressure $P_F$, the pump stroke, and the number of pump strokes per unit time. In addition, correction factors for the anesthetic vapor volume delivered can be calculated with the delivery pressure $P_F$ corresponding to the gas laws known from classical thermodynamics. To do so, it is useful to relate the delivery pressure $P_F$ either to the beginning of the ejection phase or to the end of the suction phase.

In an advantageous embodiment, an anesthetic gas sensor, which measures the carrier gas stream actual value $C_I$ and sends it to an anesthetic gas regulator, is provided in the carrier gas stream downstream of the junction of the delivery tube with the anesthetic gas line. The anesthetic gas regulator is connected to the control unit and is able both to receive control signals from this and to send control signals to the control unit.

It is advantageous not to actuate the metering valve via the control unit, but to actuate the metering valve via the anesthetic gas regulator and to set the concentration of the anesthetic vapor in the carrier gas stream with the measured concentration actual value $C_I$. In this case, the control signal present in the control unit for the metering valve is simply a plausibility check value for the anesthetic gas regulator. This plausibility comparison may be performed, e.g., in the control unit. If the plausibility comparison reveals an unacceptable deviation, the control unit blocks the anesthetic gas controller and switches the metering valve over to the closed position.

It is advantageous to insert an emergency shutoff valve, which switches over to the closed position when a concentration limit value $C_G$ in the carrier gas stream is reached, as a safety device in the delivery line, behind the metering valve in the direction of flow. The emergency shutoff valve makes shutting off possible when the metering valve is jammed in the open position.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
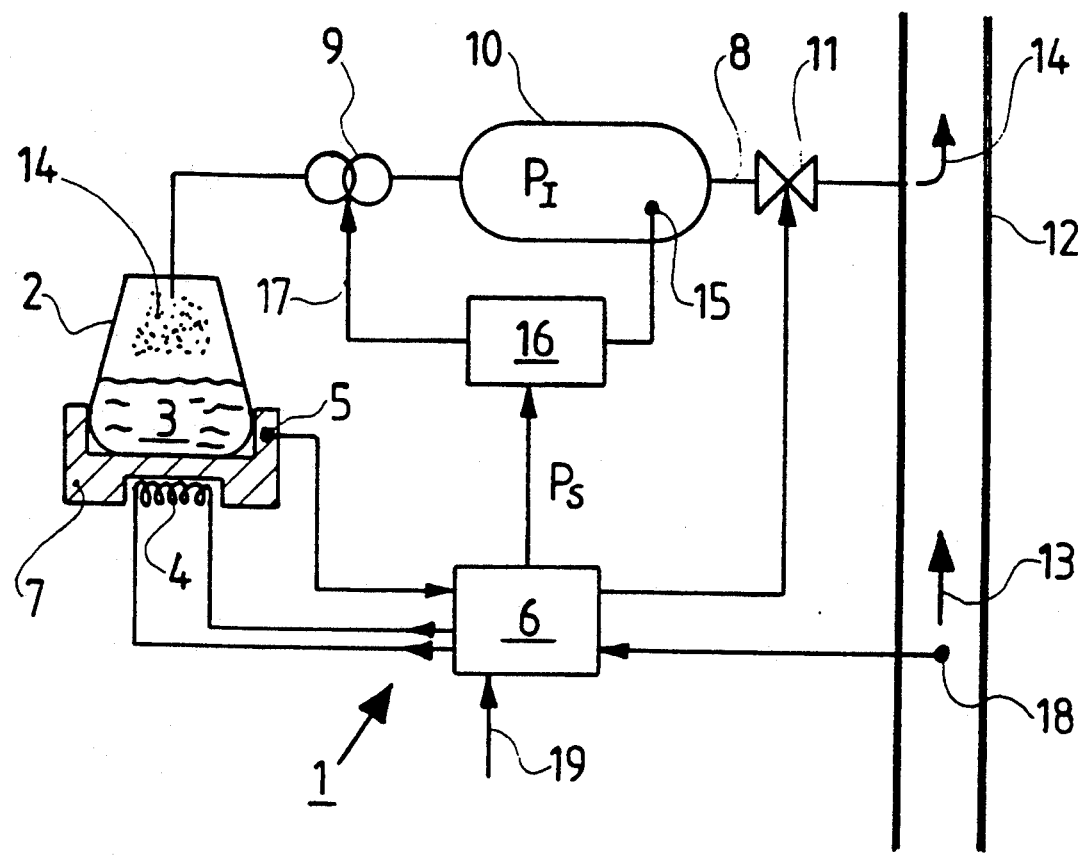
FIG. 1 is a schematic representation of a first anesthetic metering device with a pump and a buffer volume.

The first anesthetic metering device 1 shown in FIG. 1 comprises a vaporizer chamber 2, which is filled with liquid anesthetic 3 and is temperature-stabilized at a temperature T by means of a heat exchanger 7. The heat exchanger 7 has a heating coil 4 and a temperature sensor 5. The vaporizer chamber 2 is modularly inserted into the heat exchanger 7 and can be removed from it, e.g., to fill in anesthetic 3.

The heating coil 4 is supplied by a control unit 6 and, at the same time, the actual value of the temperature T in the vaporizer chamber 2, measured with the temperature sensor 5, is measured in the control unit 6 and compared with a temperature set value stored in the control unit 6. In the case of a deviation between the temperature T and the temperature set value, the heating capacity is accordingly adjusted by the control unit 6. Since this temperature T is approximately in the range of the ambient temperature, the heat exchanger 7 alone is also sufficient, in most cases, for temperature stabilization to directly feed the ambient heat into the vaporizer chamber 2. Should the temperature T drop substantially as a consequence of the removal of a rather large amount of anesthetic vapor 14, compensating heating may correspondingly be performed with the heating coil 4.

A delivery line 8 leads from the vaporizer chamber 2 via a pump 9, a buffer volume 10, and a metering valve 11 to an anesthetic gas line 12, through which a carrier gas stream 13 flows. The anesthetic vapor 14 located above the anesthetic 3 is pumped by the pump 9 out of the vaporizer chamber 2, and adjusted in the buffer volume 10 to the metering pressure $P_I$. The metering pressure $P_I$ is measured by a pressure transducer 15, and the measured signal is sent to a metering pressure regulator 16, in which it is compared with a metering pressure set value $P_s$ sent by the control unit 6. Corresponding to the deviation between $P_I$ and $P_s$, the pump 9 is brought via line 17 to constant metering pressure $P_I$. To meter anesthetic vapor 14 into the carrier gas stream 13, the metering valve 11 is switched by the control unit 6 to the open position at defined time intervals. The concentration of the anesthetic vapor 14 in the carrier gas stream 13 can be determined from the volume flow $V_I$ of the carrier gas stream 13 per unit time, which is measured with the volume measuring sensor (volume rate of flow sensor) 18, from the metering pressure $P_I$, the degree of opening and the opening time t of the metering valve 11. Corresponding preset concentration values can be sent to the control unit 6 via the signal line 19. The control unit 6 contains a microprocessor and a permanent memory, with which the calculations necessary for metering can be performed.

Figure 2:
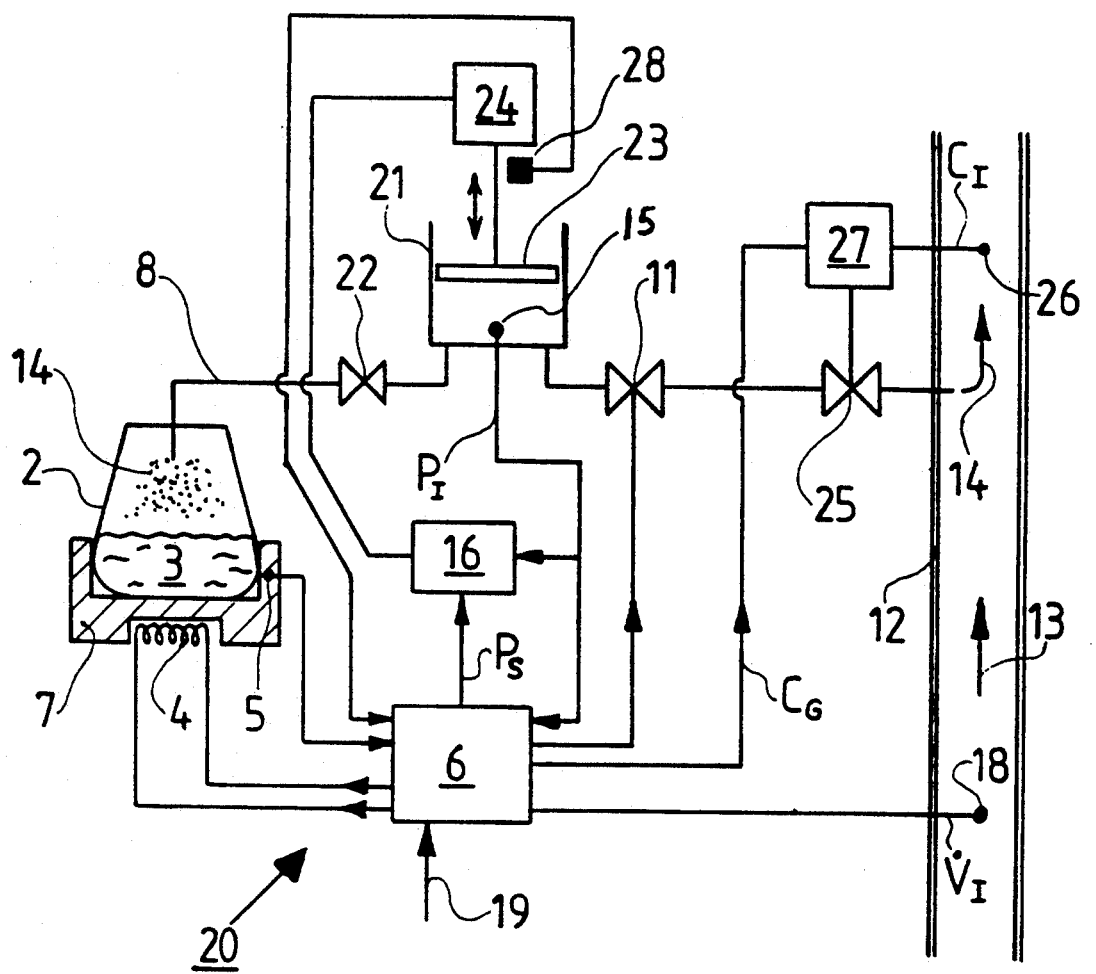
FIG. 2 is a schematic representation of a second anesthetic metering device with a piston pump.

FIG. 2 shows a second anesthetic metering device 20. Identical components are designated by the same reference numerals as in FIG. 1. Compared with the first anesthetic metering device 1 shown in FIG. 1, the pump 9 and the buffer volume 10 were replaced with a piston pump 21 with an intake valve 22 and a pump part 23 performing stroke movements for sucking in and ejecting the anesthetic vapor 14. The pump part 23 performing stroke movements is operated by a pump drive 24, which in turn is actuated by the metering pressure regulator 16.

Furthermore, an emergency shutoff valve 25, which blocks the delivery line 8 when a concentration limit value $C_G$ of the anesthetic vapor 14 is reached in the carrier gas stream 13 in the anesthetic gas line 12, is provided between the metering valve 11 and the anesthetic gas line 12. To achieve this, a concentration actual value $C_I$ is measured with an anesthetic gas sensor 26 and is compared in an anesthetic gas regulator 27 with the concentration limit value $C_G$ sent by the control unit 6. If the concentration actual value $C_I$ is equal to or higher than the concentration limit value $C_G$, the anesthetic gas regulator 27 switches the emergency shutoff valve 25 to the closed position.

The anesthetic vapor 14 is metered into the carrier gas stream 13 so that anesthetic vapor 14 is first drawn in by means of the pump part 23 performing stroke movements and the pump drive 24 via the intake valve 22, designed as a directional valve, and compressed to the metering pressure $P_I$ (as measured by pressure transducer 15) within the piston pump 21 during the ejection phase. The metering pressure $P_I$ is compared with the metering pressure set value $P_s$ in the metering pressure regulator 16, and a regulated quantity signal for the pump drive 24 is generated from the difference between $P_s$ and $P_I$.

The concentration ratio of the anesthetic vapor 14 to the carrier gas stream 13 is obtained from the volume flow $V_I$ of the carrier gas stream, the metering pressure $P_I$, the degree of opening and the opening time t of the metering valve 11.

According to an alternative mode of operation of the second anesthetic metering device 20, metering is performed not solely on the basis of the metering pressure $P_I$ and the opening time t, but on the basis of the volume delivered by the movable pump part 23. To do so, the metering valve 11 is controlled by the control unit 6 so that it is in the closed position during the suction phase and in the open position during the ejection phase. The pump stroke is measured by a displacement transducer 28 and sent to the control unit. The pump drive 24 delivers the anesthetic vapor 14 from the vaporizer chamber 2 and feeds it into the anesthetic gas line 12 according to predefined time intervals. The delivery pressure $P_F$ in the piston pump is measured with the pressure transducer 15 and sent to the control unit 6, in which correction factors for the anesthetic vapor volume delivered are calculated corresponding to the gas laws known from classical gas dynamics. To calculate the correction factors, it is advantageous to relate the delivery pressure $P_F$ to a fixed point in time, e.g., to the beginning of the ejection phase or the end of the suction phase.

Mixed forms of dosage may also be realized with the second anesthetic metering device 20, e.g., by emptying the anesthetic vapor 14 present in the piston pump 21 stepwise. The anesthetic vapor volume metered per individual step is obtained from the partial stroke of the movable pump part 23, from the partial displacement measured with the displacement transducer 28, and the metering delivery pressure $P_w$ at the end of the respective partial ejection phase.

Figure 3:
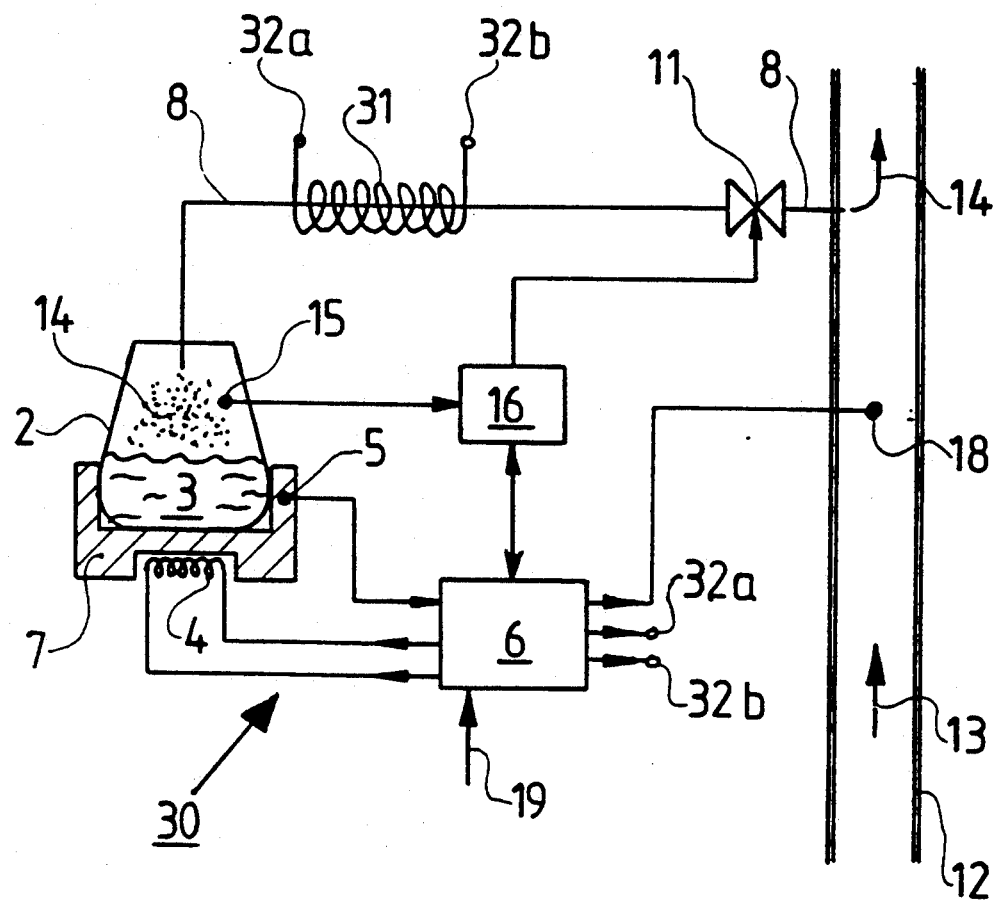
FIG. 3 is a schematic representation of a third anesthetic metering device with direct metering from the vaporizer chamber.

FIG. 3 shows a third anesthetic metering device 30, in which the anesthetic vapor 14 is metered directly from the reservoir 2. Identical components are designated by the same reference numerals as in FIG. 1 and FIG. 2. Compared with the first anesthetic metering device 1 shown in FIG. 1, the metering pressure $P_I$ is generated by heating the vaporizer chamber 2 by means of the heater 4 rather than by the pump 9. The pressure of the anesthetic vapor 14 is adjusted so that it is a few 100 mbar higher than the ambient pressure. The metering pressure $P_I$ is measured with the pressure transducer 15 within the vaporizer chamber 2 and is processed by the metering pressure regulator 16. To prevent the anesthetic vapor 14 from condensing, a heating coil 31, whose terminals 32a, 32b are connected to the control unit 6, is provided in the delivery line section 8.

While specific embodiments of the invention have been shown and described in detail to illustrate the application of the principles of the invention, it will be understood that the invention may be embodied otherwise without departing from such principles.

What is claimed is:

1. An anesthetic metering device, comprising:
a temperature-stabilized anesthetic vaporizer chamber partially filled with liquid anesthetic to define an anesthetic vapor source;
a carrier gas stream into which anesthetic vapor is to be metered;
a single delivery line with a metering valve, said delivery line being connected to said carrier gas stream and being connected to said vaporizer chamber providing the only communication between said vaporizer chamber and said carrier gas stream;
control means for controlling said metering valve; and
gas delivery pumping means positioned in said delivery line for conveying anesthetic vapor from said vaporizer chamber and generating a metering pressure $P_I$, for delivery of anesthetic vapor at said metering pressure $P_I$ to said delivery line upstream of said metering valve.

2. A anesthetic metering device according to claim 1, wherein said gas delivery pumping means comprises a pump and a buffer volume, said buffer volume being located downstream of said pump and a pressure transducer for detecting said metering pressure $P_I$, said pressure transducer being provided in said buffer volume, said control means including a metering pressure regulator and a control unit, said control unit providing a pressure set value $P_s$ to said metering pressure regulator and said metering pressure regulator forming a difference between said metering pressure $P_I$ and said metering pressure set value $P_s$ to form a metering pressure regulated quantity signal for regulating said pump.

3. An anesthetic metering device according to claim 1, wherein said gas delivery pumping means is a piston pump with an intake valve in a suction portion of said delivery line and including a pump part performing a stroke movement for delivering anesthetic vapor, said pump part being attached to a pump drive for generating said metering pressure $P_I$.

4. An anesthetic metering device according to claim 1, wherein said carrier gas stream is provided in an anesthetic gas line, said delivery line being connected to said anesthetic gas line at a delivery line junction, an anesthetic gas sensor for measuring an actual concentration value $C_I$ is positioned in said carrier gas stream, said anesthetic gas sensor being connected to anesthetic gas regulator means for comparing said actual concentration value $C_I$ to a concentration limit $C_G$.

5. An anesthetic metering device according to claim 4, wherein said metering valve is connected to said anesthetic gas regulator for actuation of said metering valve by said anesthetic gas regulator, said control means for forming a control signal for said metering valve which is a plausibility check value for metering.

6. An anesthetic metering device according to claim 4, further comprising an emergency shut-off valve switchable between a closed position and an open position, said emergency shut-off valve being switched to said closed position upon said anesthetic gas sensor detecting a gas concentration above a limit value $C_g$, said emergency shut-off valve being connected to said delivery line for closing off said delivery line at a location downstream of said metering valve.

7. An anesthetic metering device according to claim 1, wherein said gas delivery means comprises a heating arrangement for generating anesthetic vapor of said metering pressure $P_I$.

8. An anesthetic metering device according to claim 2, wherein said pump is a bellows pump.

9. An anesthetic metering device according to claim 2, wherein each of said buffer volume and said pump are provided as modular unit means for connection into said delivery line and disconnection from said delivery line.

10. An anesthetic metering device, comprising:
chamber means defining a chamber partially filled with liquid anesthetic and including a vapor anesthetic space, above said liquid anesthetic;
temperature stabilization means for establishing a liquid anesthetic temperature of liquid anesthetic in said chamber means, said temperature stabilization means including a heat exchanger for stabilizing temperature of said liquid anesthetic to ambient temperature and heating means for heating said liquid anesthetic, said temperature stabilization means for stabilizing said liquid anesthetic to a temperature providing vapor anesthetic in said vapor anesthetic space;

carrier gas stream means including a carrier gas inlet and a carrier gas outlet;

single delivery line means connected to said carrier gas stream and connected to said chamber means providing the only communication between said chamber means and said carrier gas stream means for supplying said carrier gas stream with vapor anesthetic, said delivery line means including a metering valve;

control means for controlling said metering valve; and gas delivery means positioned in said delivery line for conveying anesthetic vapor from said vapor anesthetic space of said chamber means and generating a metering pressure $P_I$ for delivery of anesthetic vapor at said metering pressure $P_I$ to said delivery line, upstream of said metering valve.

11. An anesthetic metering device according to claim 10, wherein said gas delivery means comprises a pump and a buffer volume, said buffer volume being located downstream of said pump and a pressure transducer for detecting said metering pressure $P_I$, said pressure transducer being provided in said buffer volume, said control means including a metering pressure regulator and a control unit, said control unit providing a pressure set value $P_s$ to said metering pressure regulator and said metering pressure regulator forming a difference between said metering pressure $P_I$ and said metering pressure set value $P_s$ to form a metering pressure regulated quantity signal for regulating said pump.

12. An anesthetic metering device according to claim 10, wherein said gas delivery means includes a piston pump with an intake valve in a suction portion of said delivery line and including a pump chamber and a pump part performing a stroke movement for delivering anesthetic vapor in said pump chamber, said pump part being attached to a pump drive, and a pressure transducer for detecting a metering pressure $P_I$ in said pump chamber, said control means including a metering pressure regulator and a control unit, said control unit providing a pressure set value $P_s$ to said metering pressure regulator and said metering pressure regulator forming a difference between said metering pressure $P_I$ and said metering pressure set value $P_s$ to form a metering pressure regulated quantity signal for regulating said pump drive.

13. An anesthetic metering device according to claim 1, wherein said gas delivery means comprises a pressure transducer for detecting said metering pressure $P_I$, said pressure transducer being provided in said buffer volume, control means including a metering pressure regulator and a control unit, said control unit activating said heating means until said metering pressure $P_I$ is equal to a pressure set value $P_s$.

14. An anesthetic metering device according to claim 13, further comprising volume rate of flow sensor means positioned in said carrier gas stream for generating a volume rate of flow signal, said control means receiving said volume rate of flow signal and controlling said metering valve to obtain a predetermined concentration of anesthetic vapor in said carrier gas stream, based on said volume rate of flow and said anesthetic vapor provided at said metering pressure $P_I$.

15. An anesthetic metering device according to claim 13, further comprising volume rate of flow sensor means positioned in said carrier gas stream for generating a volume rate of flow signal, said control means receiving said volume rate of flow signal and controlling said metering valve to obtain a predetermined concentration of anesthetic vapor in said carrier gas stream, based on said volume rate of flow and said anesthetic vapor provided at said metering pressure $P_I$.

16. An anesthetic metering device according to claim 11, further comprising volume rate of flow sensor means positioned in said carrier gas stream for generating a volume rate of flow signal, said control means receiving said volume rate of flow signal and controlling said metering valve to obtain a predetermined concentration of anesthetic vapor in said carrier gas stream, based on said volume rate of flow and said anesthetic vapor provided at said metering pressure $P_I$.

* * * * *